United States Patent
Petroelje

(10) Patent No.: US 12,427,243 B2
(45) Date of Patent: Sep. 30, 2025

(54) PORTABLE ENTERAL FEEDING BAG HOLDER

(71) Applicant: Taylor Petroelje, Holland, MI (US)

(72) Inventor: Taylor Petroelje, Holland, MI (US)

( * ) Notice: Subject to any disclaimer, the term of this patent is extended or adjusted under 35 U.S.C. 154(b) by 0 days.

(21) Appl. No.: 18/212,785

(22) Filed: Jun. 22, 2023

(65) Prior Publication Data

US 2024/0131251 A1 Apr. 25, 2024
US 2024/0226420 A9 Jul. 11, 2024

Related U.S. Application Data

(60) Provisional application No. 63/418,094, filed on Oct. 21, 2022.

(51) Int. Cl.
  *A61M 5/14* (2006.01)

(52) U.S. Cl.
  CPC ........ *A61M 5/1417* (2013.01); *A61M 5/1415* (2013.01)

(58) Field of Classification Search
  CPC .. A61M 5/1417; A61M 5/1415; A61M 5/008; A61M 2209/084; A61M 2209/086; A61J 1/10; A61J 15/011; A61J 15/0015; A61J 15/0076; A61J 15/0026
  USPC ...... 248/317, 146, 312; 604/257; 222/181.2; 211/60.1, 62, 68, 70.2, 70.5, 70.6, 70.8
  See application file for complete search history.

(56) References Cited

U.S. PATENT DOCUMENTS

| | | | | |
|---|---|---|---|---|
| D119,320 S | * | 3/1940 | Katcher | D6/682 |
| 2,590,154 A | | 3/1952 | Burns et al. | |
| 3,165,241 A | * | 1/1965 | Curry | A61J 15/0011 215/11.1 |
| D260,432 S | * | 8/1981 | Kadar | D24/128 |
| D269,751 S | * | 7/1983 | Rieman | D6/682.4 |
| D307,182 S | * | 4/1990 | Smith | D24/128 |
| 5,386,958 A | * | 2/1995 | Amato | A61J 15/0026 248/150 |
| D357,824 S | * | 5/1995 | Chan | D6/682 |
| 5,470,037 A | * | 11/1995 | Willis | A61J 9/0638 248/409 |
| 5,494,087 A | * | 2/1996 | Pitelka | B65B 3/003 141/2 |
| 6,135,983 A | * | 10/2000 | Andrews | A61J 1/16 604/257 |
| D508,771 S | * | 8/2005 | Gibson | D3/259 |

(Continued)

FOREIGN PATENT DOCUMENTS

WO 2017171748 A1 10/2017
WO 2019112429 A1 6/2019

*Primary Examiner* — Ingrid M Weinhold

(74) *Attorney, Agent, or Firm* — WARNER NORCROSS + JUDD LLP

(57) ABSTRACT

A portable feeding bag holder for an enteral feeding bag is provided. The portable feeding bag holder includes a planar base having upper and lower surfaces. A cradle for receiving an enteral pump is disposed on the upper surface of the base. A frame extends upwardly from the base. A transverse bracket member extends across the frame and is spaced from the base. The bracket member includes a support including at least one receiver for suspending an enteral feeding bag therefrom. A handle is disposed at a distal end of the frame opposite the base. A method of transporting an enteral feeding bag is also provided.

18 Claims, 10 Drawing Sheets

(56) References Cited

U.S. PATENT DOCUMENTS

| | | | |
|---|---|---|---|
| 6,969,031 B2 * | 11/2005 | Ugent | A61M 5/1415 248/129 |
| D518,893 S * | 4/2006 | Ugent | D24/128 |
| 7,040,681 B1 * | 5/2006 | Broberg | B25H 3/04 294/146 |
| D622,377 S * | 8/2010 | Jackson | D24/128 |
| 10,046,108 B2 * | 8/2018 | Nesler | A61M 5/1417 |
| 10,455,923 B1 | 10/2019 | Domingues et al. | |
| 10,874,791 B2 * | 12/2020 | Mager | A61M 5/1415 |
| 10,898,639 B1 * | 1/2021 | Lamb | A61M 5/008 |
| D980,974 S * | 3/2023 | O'Donnell | D24/128 |
| 11,806,508 B1 * | 11/2023 | Denkovich | A61M 5/1782 |
| 2004/0262463 A1 * | 12/2004 | Jackson | F16L 3/003 248/121 |
| 2005/0040126 A1 * | 2/2005 | Gaster | A61M 5/1415 211/207 |
| 2010/0057017 A1 * | 3/2010 | Pappas | A61M 5/1417 604/257 |
| 2010/0282807 A1 | 11/2010 | Sisk et al. | |
| 2012/0175325 A1 * | 7/2012 | Del Grippo | A47B 96/021 211/59.4 |
| 2016/0263310 A1 * | 9/2016 | Helbig | F16M 11/041 |
| 2016/0317392 A1 * | 11/2016 | Harris | F16M 11/046 |
| 2019/0381929 A1 | 12/2019 | Millett et al. | |
| 2021/0205553 A1 * | 7/2021 | Salmon | A61M 16/0003 |
| 2022/0111141 A1 | 4/2022 | Millar | |
| 2023/0263692 A1 * | 8/2023 | Purdue | A61H 3/04 280/87.021 |

* cited by examiner

PORTABLE ENTERAL FEEDING BAG HOLDER

CROSS REFERENCE TO RELATED APPLICATIONS

This application claims the benefit of U.S. Provisional Application No. 63/418,094, filed Oct. 21, 2022, the disclosure of which is incorporated by reference in its entirety.

FIELD OF THE INVENTION

The disclosure generally relates to bag holders and, more specifically, to enteral feeding bag holders that provide for the holding of enteral feeding bags.

BACKGROUND OF THE INVENTION

Enteral feeding refers to the intake of nourishment via the gastrointestinal (GI) tract, which includes the mouth, esophagus, stomach, and intestines. A person with a medical condition that encumbers or prevents eating of food and drinking of liquids via the mouth is typically nourished through a feeding tube that extends from a feeding bag containing the nourishment (in the form of a liquid or a solid-liquid mixture) to the person's stomach or small intestine. As the person might need to receive nourishment and hydration from a feeding bag multiple times a day, it is apparent that use of a feeding bag may severely restrict this person's mobility.

For example, it is known in the art relating to enteral feeding bags to carry the feeding bags on an IV stand having a pole that extends vertically from a base having a plurality of legs on each of which is mounted a wheel. One or more hooks are disposed at the top of the pole from which the feeding bag is hung. However, these IV stands are cumbersome to maneuver as they must be wheeled on a floor around beds, chairs, tables, and other furniture present in the room in which the IV stand is disposed. Also, due to the size and height of these IV stands, it is difficult to move one of the IV stands from one floor of a building to another, and even less desirable to move the IV stand from one building to another (for example, to transport the IV stand from one residence to another).

Further, the contents of feeding bags are typically fed to a patient using an enteral pump that pumps the contents from the feeding bag through feeding tubes to the patient. However, IV stands do not have a mount for the enteral pump, and therefore if a patient wants to move the IV stand during or between uses, the patient or an aide must carry the enteral pump in addition to wheeling the IV stand along a floor. This drawback further complicates the movement of the IV stand especially when needing to move the feeding location for the patient from one room or residence to another. Furthermore, the length of feeding tubes required for use of feeding bags with IV stands, which are typically 5 to 7 feet in height, increases the possibility that the feeding tubes become tangled with the wheels and legs of the base during rolling movement of the IV stand. The length of feeding tube dangling from the IV bags also present a tripping hazard when walking with the IV stand.

BRIEF SUMMARY OF THE INVENTION

An improved portable feeding bag holder for an enteral feeding bag is provided. The portable feeding bag holder includes a planar base having upper and lower surfaces. A cradle for receiving an enteral pump is disposed on the upper surface of the base. A frame extends upwardly from the base. A transverse bracket member extends across the frame and is spaced from the base. The bracket member includes a support including at least one receiver for suspending an enteral feeding bag therefrom. A handle is disposed at a distal end of the frame opposite the base.

In specific embodiments, the bracket member is adjustable along the frame towards and away from the base.

In specific embodiments, the support includes two receivers.

In particular embodiments, the receivers are positioned towards a front and a back of the feeding bag holder.

In particular embodiments, the receivers are aligned in a direction perpendicular to a transverse direction across the frame.

In specific embodiments, each receiver is an opening in the support.

In particular embodiments, each receiver is defined by a semi-circular slot.

In particular embodiments, the opening is sized to have a diameter that is smaller than a diameter of a collar of the enteral feeding bag.

In specific embodiments, the base is weighted.

In specific embodiments, the portable feeding bag holder further includes a tube holder disposed on a side of the frame.

In particular embodiments, the tube holder is a hook.

In particular embodiments, the tube holder includes a slot facing away from the base.

In specific embodiments, the lower surface of the base includes a friction material.

In particular embodiments, the friction material is one of rubber and silicone.

In particular embodiments, the friction material on the lower surface includes an anti-slip pattern.

In specific embodiments, a length of the frame from the base to the handle is greater than a length of the bracket member in the transverse direction.

In specific embodiments, the support of the bracket member does not extend beyond a footprint of the portable feeding bag holder.

In specific embodiments, a distance from the base to the bracket member is greater than a length of the enteral feeding bag that is suspended from the support.

A method of transporting an enteral feeding bag is also provided. The method includes the step of providing a portable feeding bag holder including a planar base having upper and lower surfaces. A cradle for receiving an enteral pump is disposed on the upper surface of the base. A frame extends upwardly from the base. A transverse bracket member extends across the frame and is spaced from the base. The bracket member includes a support including at least one receiver for suspending an enteral feeding bag therefrom. A handle is disposed at a distal end of the frame opposite the base. The base of the portable feeding bag holder is positioned on a surface at a first location. The method further includes the step of lifting the portable feeding bag holder by the handle and off the surface. The method further includes the step of carrying the portable feeding bag holder by the handle to move the portable feeding bag holder from the first location to a different, second location. The method further includes the step of setting the base of the portable feeding bag holder down onto a surface at the second location.

BRIEF DESCRIPTION OF THE DRAWINGS

Various advantages and aspects of this disclosure may be understood in view of the following detailed description when considered in connection with the accompanying drawings, wherein.

DETAILED DESCRIPTION OF THE INVENTION

Figure 1:
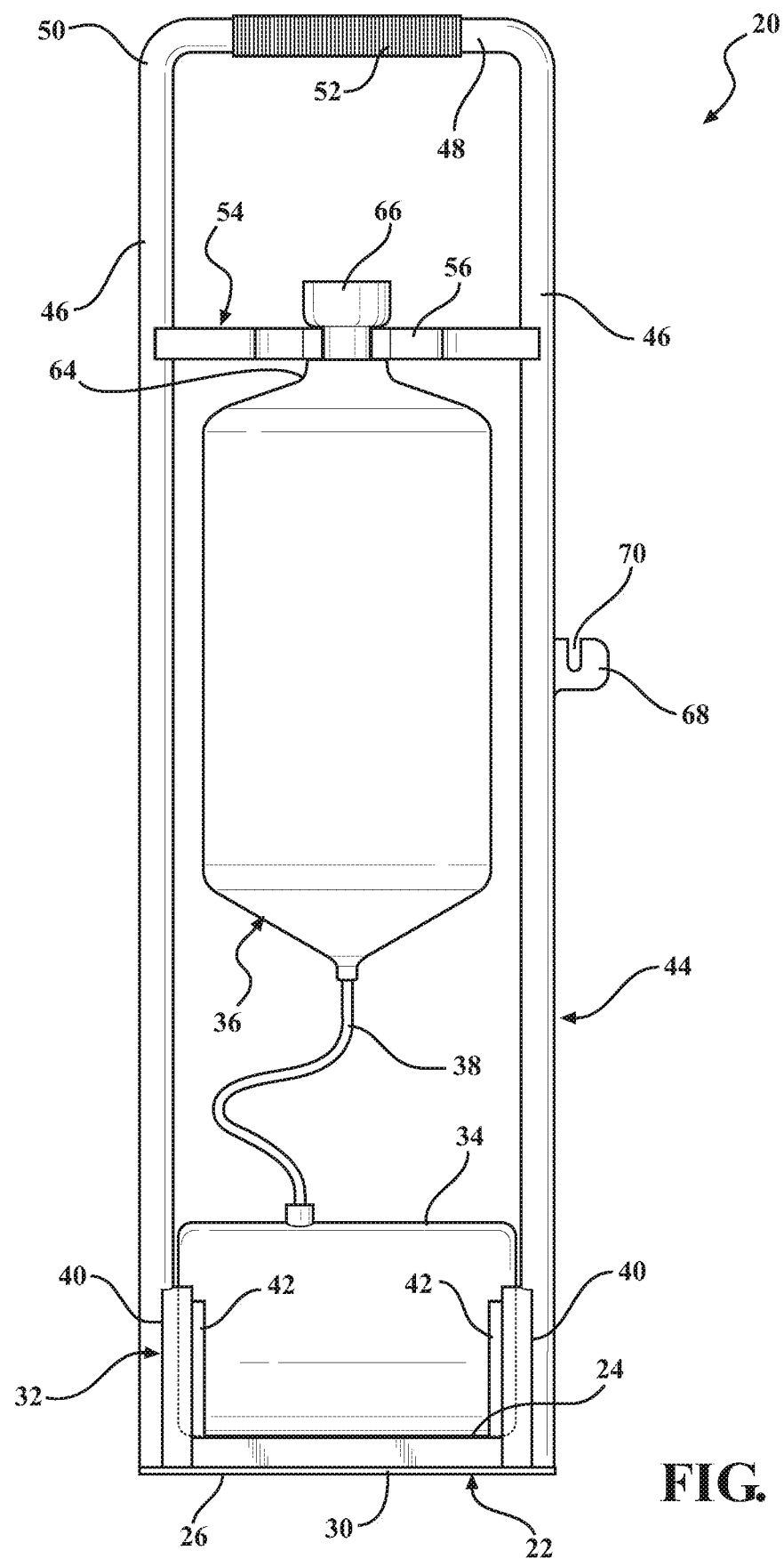
FIG. 1 is a front view of a portable feeding bag holder in accordance with some embodiments of the disclosure, the portable feeding bag holder being in an upright disposition.

A portable feeding bag holder is provided. Referring to FIGS. 1-10, wherein like numerals indicate corresponding parts throughout the several views, the portable feeding bag holder (also referred to herein as simply the bag holder) is illustrated and generally designated at 20, 120, 220. Certain features of the bag holder 20,120, 220 are functional, but can be implemented in different aesthetic configurations. References to upper, lower, vertical, horizontal, lateral, front-to-back, and transverse directions are relative to an upright disposition of the bag holder 20, 120, 220, and are otherwise not intended to be limiting. It should be understood that the orientation of the bag holder 20, 120, 220 may varied from the upright disposition, such as by resting the bag holder on its side.

With reference now to FIGS. 1-4, the bag holder 20 includes a planar base 22 having an upper surface 24 and an opposite lower surface 26. The base 22 generally extends in front-to-back and transverse (side-to-side) directions and has a length and width that are far greater than its thickness. The base 22 is delimited in the front-to-back and transverse directions by a peripheral edge 28. The base 22 may be a rectangular solid and may have a rectangular or square footprint, i.e. the upper and lower surfaces may be rectangular or square in shape. However, it should be understood that the base may have any polygonal shape and is not limited in shape to a parallelogram. The lower surface 26 of the base 22 may include a friction material 30 via which frictional forces are imparted to the base when the bag holder 20 is placed on a surface as described in greater detail below. The friction material 30 may be a rubber, silicone, or other similar slip-resistant material that can be applied to the lower surface 26. Further, the friction material 30 may alternatively or additionally include an anti-slip pattern such as found on, for example, a floormat or a sole of a shoe. Additionally, the base 22 optionally may be weighted to prevent tipping or undesired movement of the bag holder 20.

A cradle 32 is disposed on the upper surface 24 of the base 22. The cradle 32 is sized and shaped to receive an enteral pump 34 for pumping nourishment from an enteral feeding bag 36 through a feeding tube(s) 38. Thus, the cradle 32 and base surface 24 on which the cradle is disposed have a footprint that is at least as big and not much larger than that of the enteral pump 34, thus keeping the size of the base and accompanying cradle compact. In some embodiments as shown in FIGS. 1-4, the cradle 32 includes a pair of sidewalls 40 that extend vertically upward from the upper surface 24 of the base 22. The sidewalls 40 may be disposed along the transverse (left- and right-hand sides) of the base 22 and may be sized to be, for example, at least approximately half as tall as a height of the enteral pump 34. The cradle 32 may further include front and rear stops in the form of vertical studs 42 that are disposed on the inner sides of the sidewalls 40 at the front and rear corners of the base 22. The studs 42 may have the same or similar height as the sidewalls 40 while also not being taller than and not extending beyond the upper edges of the sidewalls. The studs 42 limit forward and backward movement of the enteral pump 34 when it is disposed in the cradle 32, such that the enteral pump is loaded into and out of the cradle from above.

A frame 44 extends upwardly from the base 22, and may, for example, extend from a top side of each of the sidewalls 40, or from the base along the sides of the sidewalls and beyond the sidewalls. The frame 44 may be, for example, generally tubular. For example, the frame 44 may be in the form of two vertically extending posts 46 that extend longitudinally away from the base 22. A handle 48 is disposed at a distal end 50 of the frame 44 that is opposite the base 22. The handle 48 may be a separate member that is connected between the posts 46 or alternatively may be formed (e.g. by molding) to be integral with and form a part of the frame 44. Optionally, the handle 48 may include a gripping surface (grip 52) that reduces slippage when the handle is grasped by a hand of a user during movement of the bag holder 20. The frame forms a support for other members of the bag holder 20 as described below, and forms a connection between the handle 48 and the base 22. The frame 44 is generally open such that the frame does not impede access to the cradle 32 or the upper body of the bag holder 20.

Figure 2:
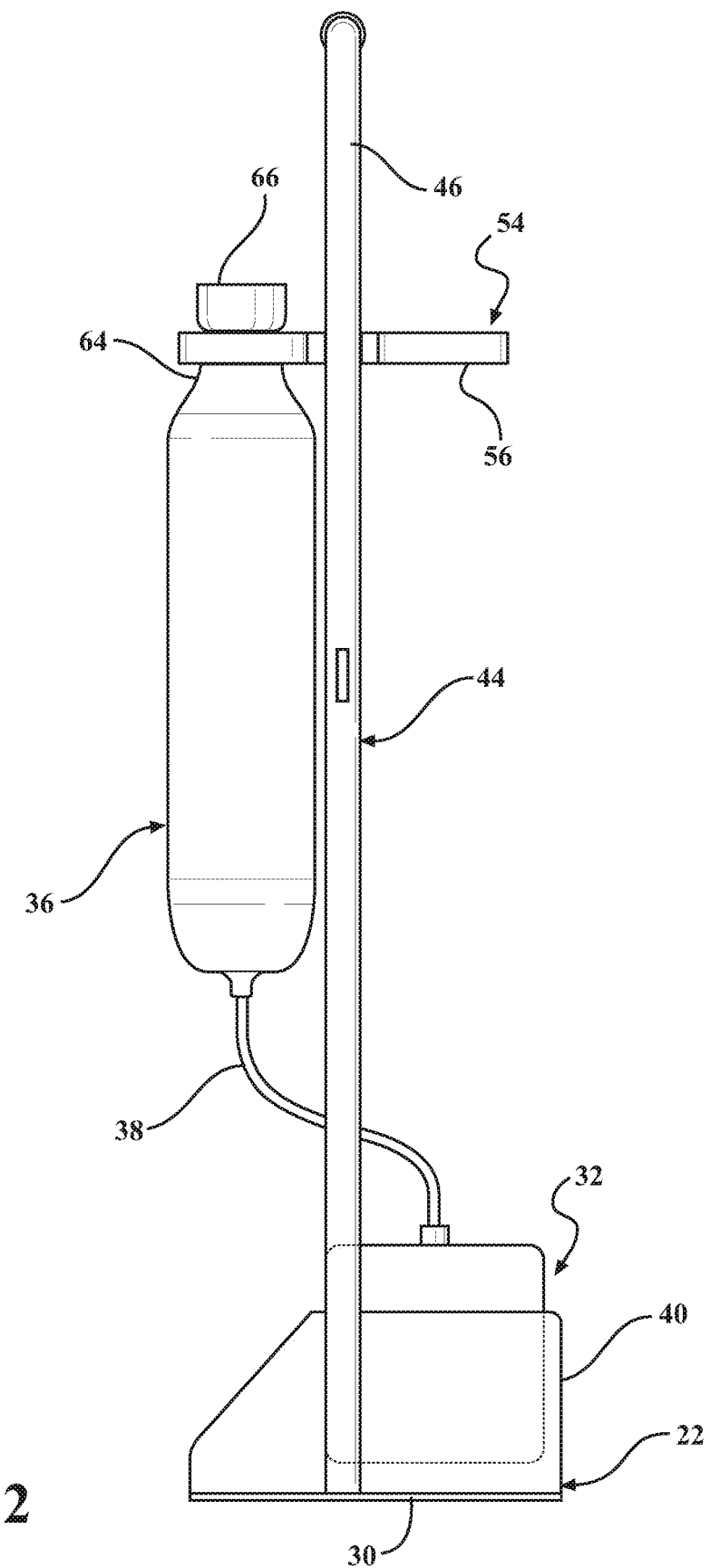
FIG. 2 is a side view of the portable feeding bag holder of FIG. 1.
Figure 3:
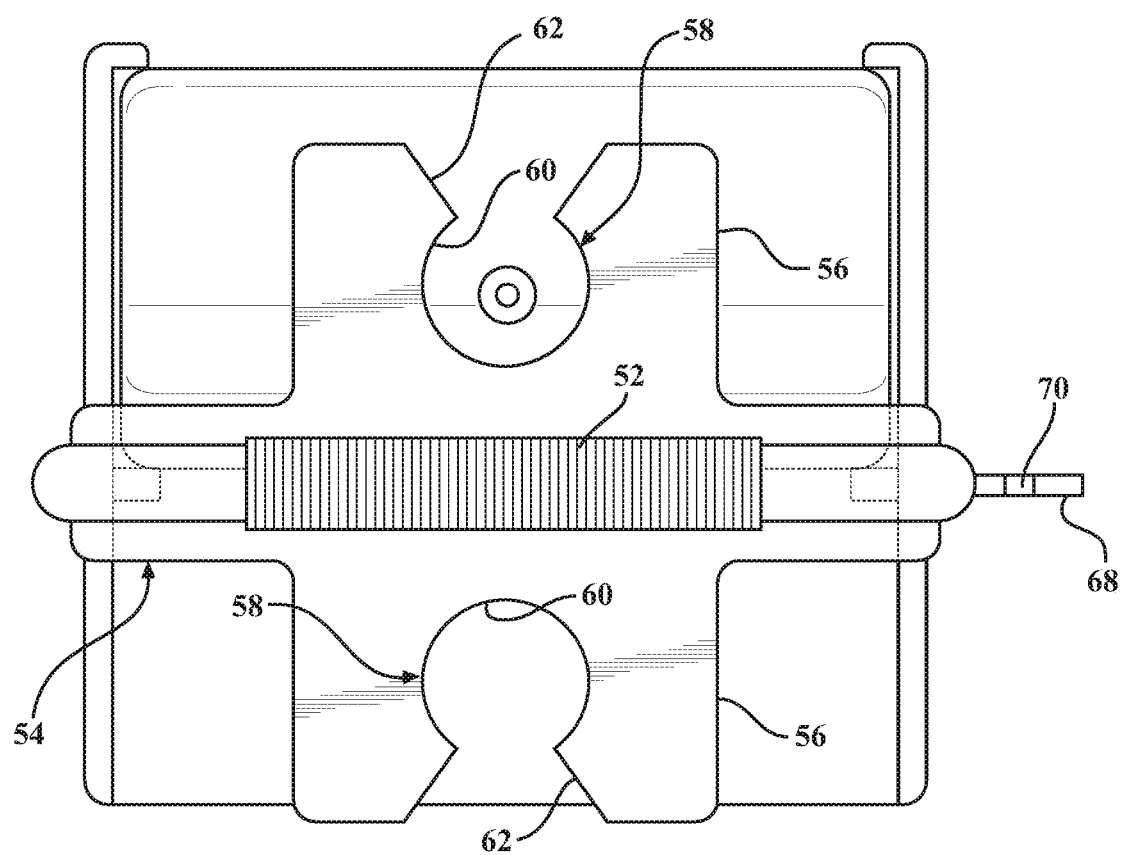
FIG. 3 is a plan view of the portable feeding bag holder of FIG. 1.
Figure 4:
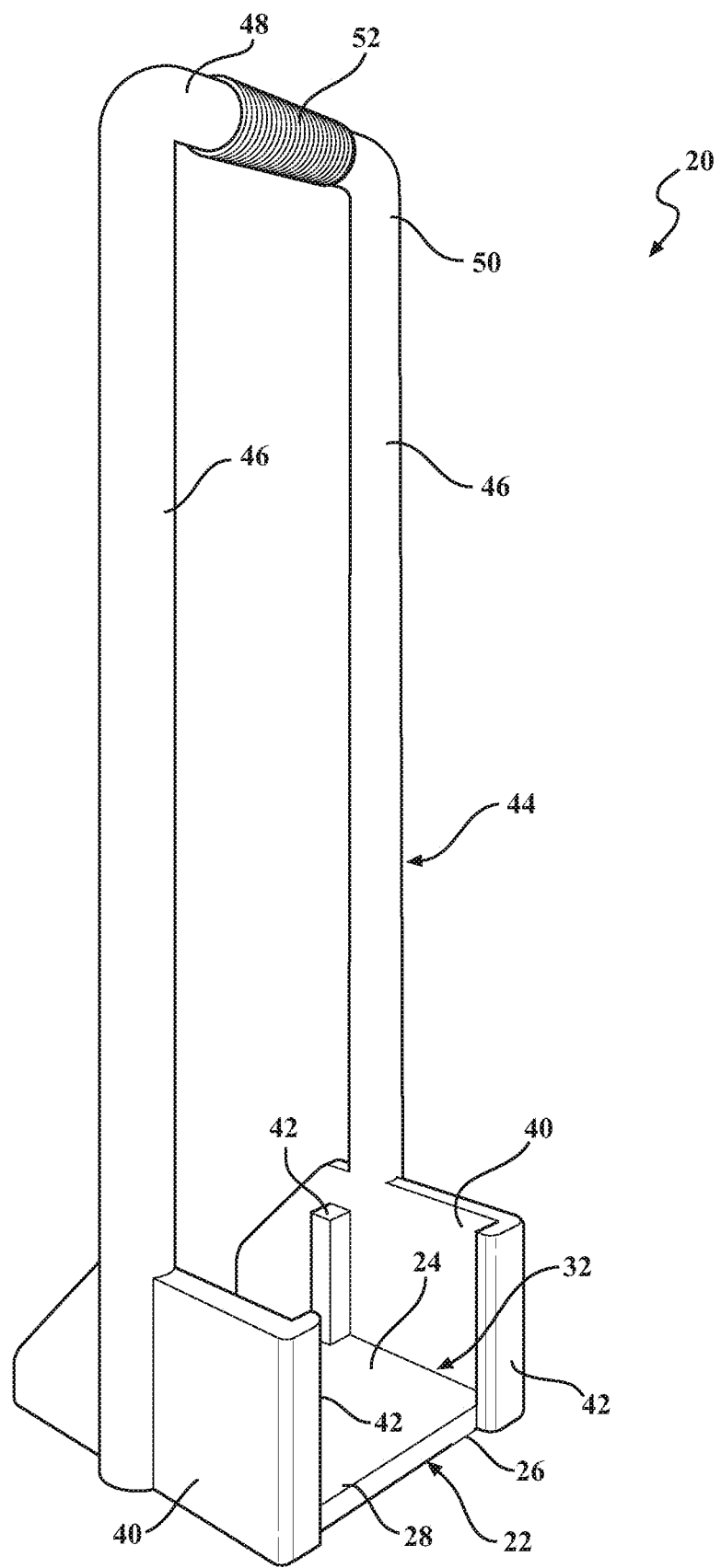
FIG. 4 is perspective view of a base, cradle, frame, and handle of the portable feeding bag holder.
Figure 5:
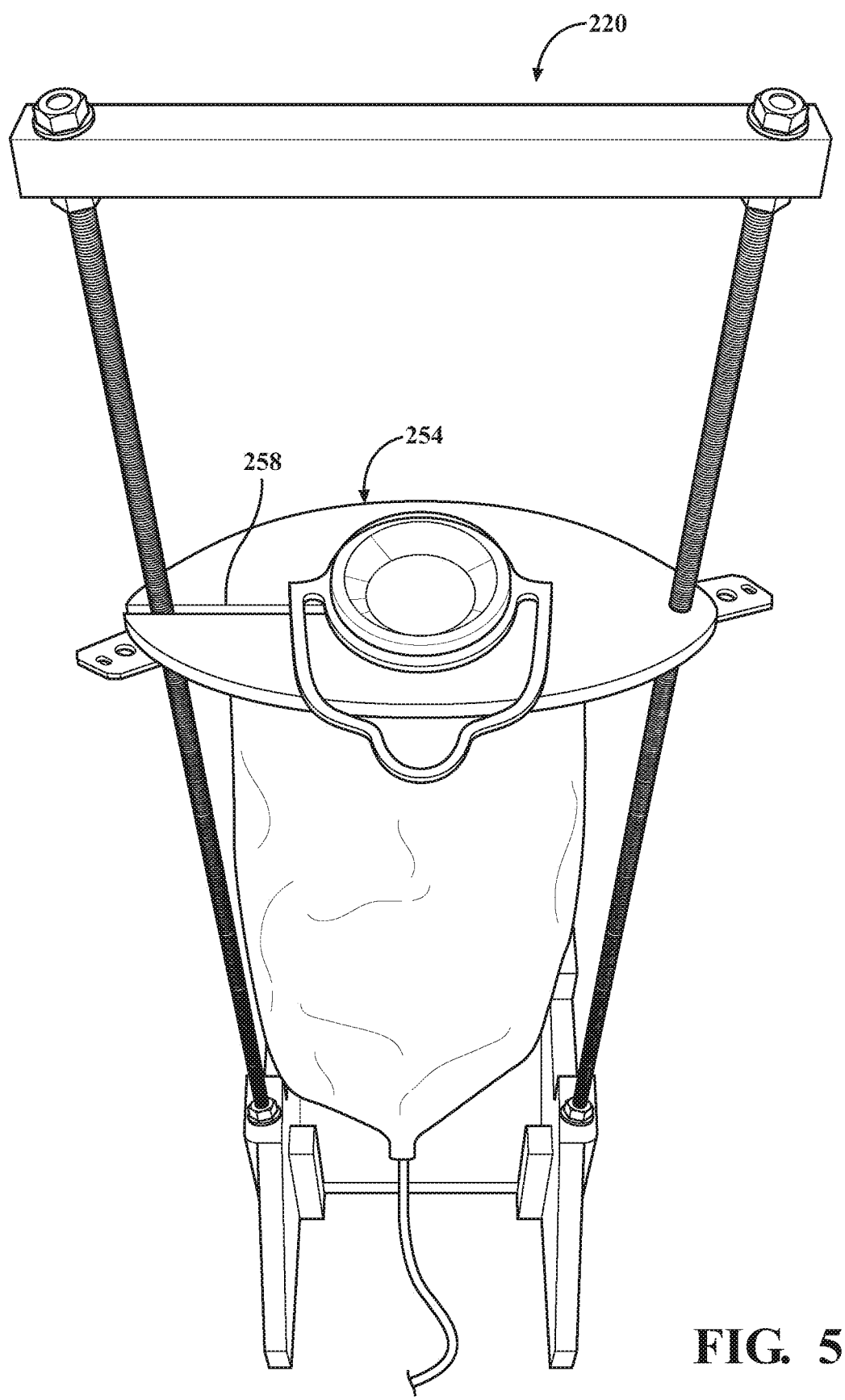
FIG. 5 is a front perspective view of a portable feeding bag holder in accordance with other embodiments of the disclosure, the portable feeding bag holder being in an upright disposition.
Figure 6:
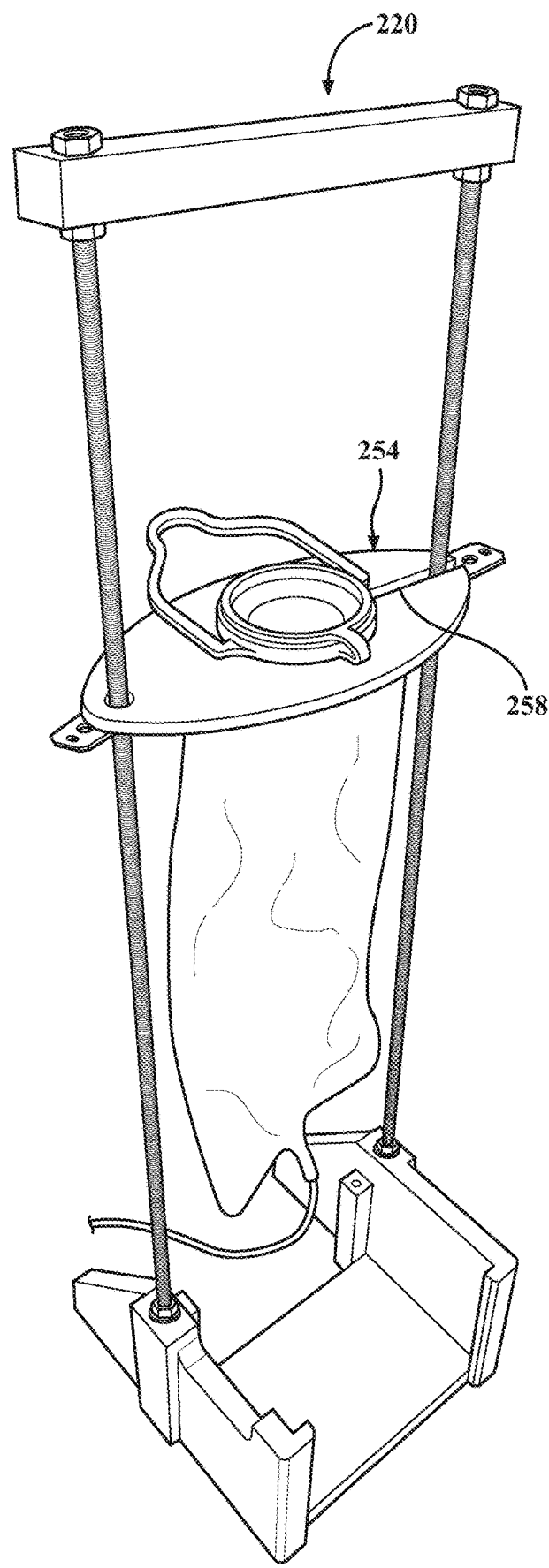
FIG. 6 is a rear perspective view of the portable feeding bag holder of FIG. 5.
Figure 7:
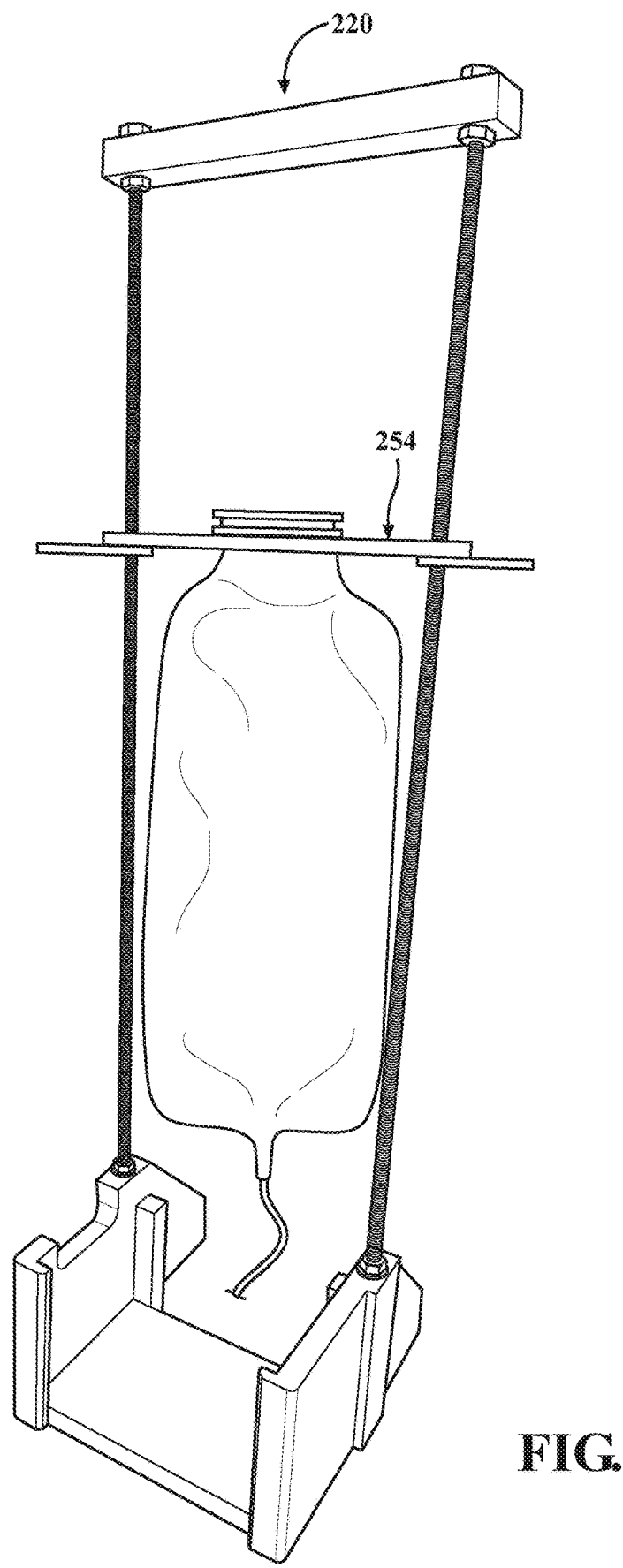
FIG. 7 is another rear perspective view of the portable feeding bag holder of FIG. 5.

A transverse bracket member 54 extends transversely from side-to-side across the frame 44 between the two posts 46 of the frame. The length of the frame 44 from the base 22 to the handle 48 is significantly greater than a length of the bracket member 54 in the transverse direction such that the bag holder 20 is taller than it is wide. The bracket member 54 is spaced from the base 22, is disposed between the base 22 and the handle 48, and is typically disposed closer to the handle than the base. The bracket member 54 may be fixed in its position between the base 22 and handle 48 as shown in FIGS. 1-3, or alternatively the height of the bracket member relative to the base may be adjustable, for example by sliding the bracket member along the frame and securing the bracket member in a desired position as shown in FIGS. 5-7. In either case, a distance from the base 22 to the bracket member 54 is set to be greater than a length of the enteral feeding bag 36 that is suspended from the bracket member 54 during use, such that the suspended feeding bag hangs above the base 22 and cradle 32. More particularly, the bracket member 54 includes a support 56 including at least one receiver 58 for suspending the enteral feeding bag 36. For example, in the embodiment of the bracket holder 220 shown in FIGS. 5-7, the bracket member 254 includes a single receiver 258, while in the embodiment shown in FIGS. 1-3, the bracket member 54 preferably includes two receivers 58. The presence of two receivers allows for two feeding bags to be simultaneously hung from the support 56, one bag which may contain food nourishment and the other bag containing water or other form of liquid hydration, for example. In the single-receiver embodiment, the receiver is generally disposed in the center of the support of the bracket member, whereas in the dual-receiver embodiment shown in FIGS. 1-3, the support 56 extends from the front of the bag holder 20 to the back, and the receivers 58 are positioned towards the front and back of the bag holder with the receivers being aligned with each other in a front-back direction that is perpendicular to the transverse direction across the frame 44. Each receiver 58 is an opening in the support 56 and may be defined by a semi-circular slot. In other words, the opening forming the receiver 58 is generally circular in shape (circular opening 60) while having a slot 62 that breaks open a portion of the circle. Further, the support 56 in which the receiver(s) 58 are formed does not extend beyond the peripheral edge 28 of the base 22 and the cradle 32 such that the suspended feeding bag(s) hang over the upper surface 24 of the base and are disposed within the footprint of the bag holder defined by the base 22 and sidewalls 40 of the cradle. This construction maintains a center of gravity that is within the footprint of the bag holder 20 in the front-to-back and transverse directions.

A typical enteral feeding bag 36 is elongated and has an opening at its bottom end from which the feeding tube 38 extends and which runs from the bag to the enteral pump 34. The top of the feeding bag 36 has a flanged extension 64 that terminates in a cylindrical-like collar 66. The feeding bag 36 is mounted into the receiver 58 by sliding the flanged portion 64 of the bag directly below the collar 66 through the slot 62 of the receiver 58 and into the circular opening 60. The collar 66 of the bag 36 is then dropped into and held in the circular opening 60. It should be understood, then, that the opening 60 of the receiver 58 is sized to have a diameter that is smaller than a diameter of the collar 66 of the feeding bag 36. The feeding bag 36 is removed from the support 56 in an opposite manner. A user simply may lift up on the collar 66 to remove the collar from the opening 60 of the receiver 58, and then slide the flanged portion 64 of the bag 46 below the collar out of the slot 62. Since the frame 44 of the bag holder 20 is open, the user has open access to the receiver 58 and can easily add or remove a bag from the receiver 58.

The bag holder 20 may optionally include a tube holder 68 that is disposed on a side of the frame 44 as shown in FIG. 1. The tube holder 68 may be in the form of a hook and may include a slot 70 that faces upwardly away from the base 22. The slot 70 is sized to receive and hold a portion of a feeding tube, such as a length of feeding tube that extends from the feeding bag 36 to an inlet of the enteral pump 34. Hence, the width of the slot 70 is nearly equal to the outer diameter of the feeding tube. The feeding tube exiting the feeding bag is part of the feeding bag (i.e., the feeding bag and this tubing are manufactured as an integral unit) and typically is long. The tube holder 68 provides for the management of the excess length of this tubing, such as by wrapping loops of the tubing onto the tube holder.

In some embodiments, the cradle 32 has a width in the transverse direction of approximately 6 inches, the base 22 has a width in the transverse direction of approximately 7.1 inches, the width between the two posts 46 of the frame 44 may be approximately 5.8 inches, the width of the feeding bag 36 that is suspended below the bracket member 54 may be approximately 5.2 inches, and the width of the gripping surface 52 of the handle 48 may be approximately 3.85 inches. Further, the bag holder 20 may have a total height of approximately 24 inches, and the bracket member 54 may be positioned approximately 4.6 inches below the handle 48 at the top end of the bag holder.

The bag holder 20 can be used to support, store, and transport an enteral feeding bag during feeding from the bag as well as between feedings. For example, a subject (e.g. patient) may desire to begin a feeding session while lying in bed. In this case, the subject may set the base 22 of the bag holder 20 on the floor or a surface of a piece of furniture such as an end table (i.e., nightstand) that is next to the bed. After the feeding session begins, the subject may decide to move to another room such as a room in which a chair is located. To move the bag holder 20 to a new location, the subject simply lifts the bag holder by the handle 48 and raises it off the floor or other surface on which it is resting. The bag holder 20 is weighted such that it resists tipping over when at rest in the upright position, but is still light enough to be easily picked up and carried when loaded with feeding bag(s) and/or an enteral pump. The subject may therefore carry the bag holder 20 by the handle 48 to move the bag holder to the new location. Since the enteral pump 34 is kept in the cradle 32 of the bag holder 20, the subject need only to carry the bag holder 20, i.e. the subject does not have to separately carry the pump. Further, due to the compact dimensions of the bag holder 20, the length of feeding tube can be made much shorter and is less of a tripping hazard than the length of tubing required for use of a conventional IV stand. The subject may then easily walk with the bag holder 20 to another room, and may in this example, sit down in a chair and set the base 22 of the bag holder onto the floor next to the chair or on a surface of a piece of furniture such as a table that is next to the chair. Therefore, it is apparent that the present bag holder 20 greatly facilitates movement of a subject during feeding. Additionally, the bag holder 20 is easily transportable between feeding sessions. Again, due to its compact dimensions and lightweight construction, a subject may easily carry the bag holder 20 including mounted feeding bag(s) and pump from one location to another. For example, the subject may carry the bag holder 20 from the subject's residence to another residence or other building at which the next feeding session will take place. Thus, it is apparent that the present bag holder 20 appreciably increases the freedom of movement of a subject that is required to be fed by a feeding tube multiple times a day. Hence, the present bag holder 20 provides a significant increase in the quality of life for those required to use a feeding tube.

Figure 8:
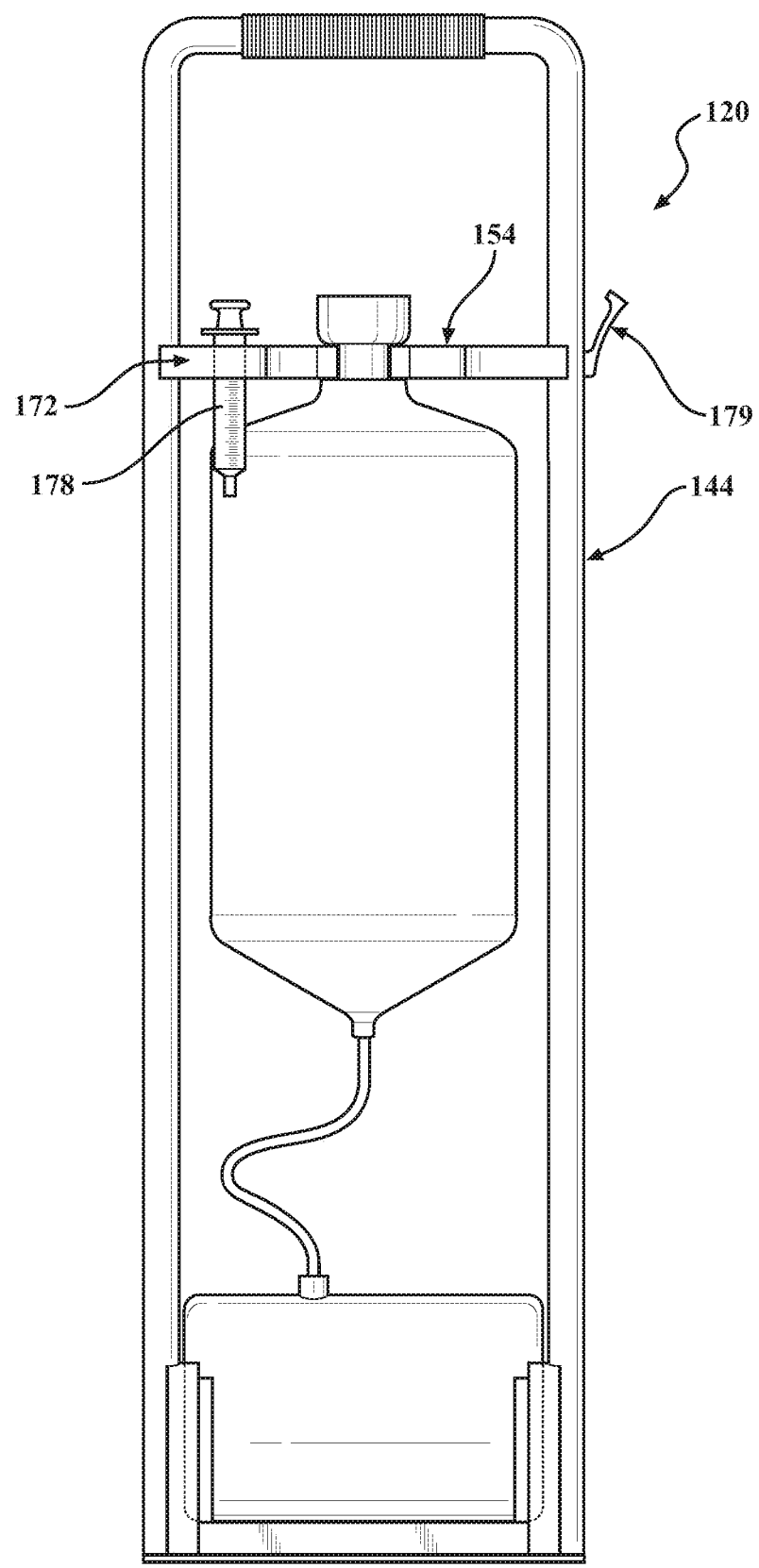
FIG. 8 is a front view of a portable feeding bag holder in accordance with yet other embodiments of the disclosure, the portable feeding bag holder being in an upright disposition.
Figure 9:
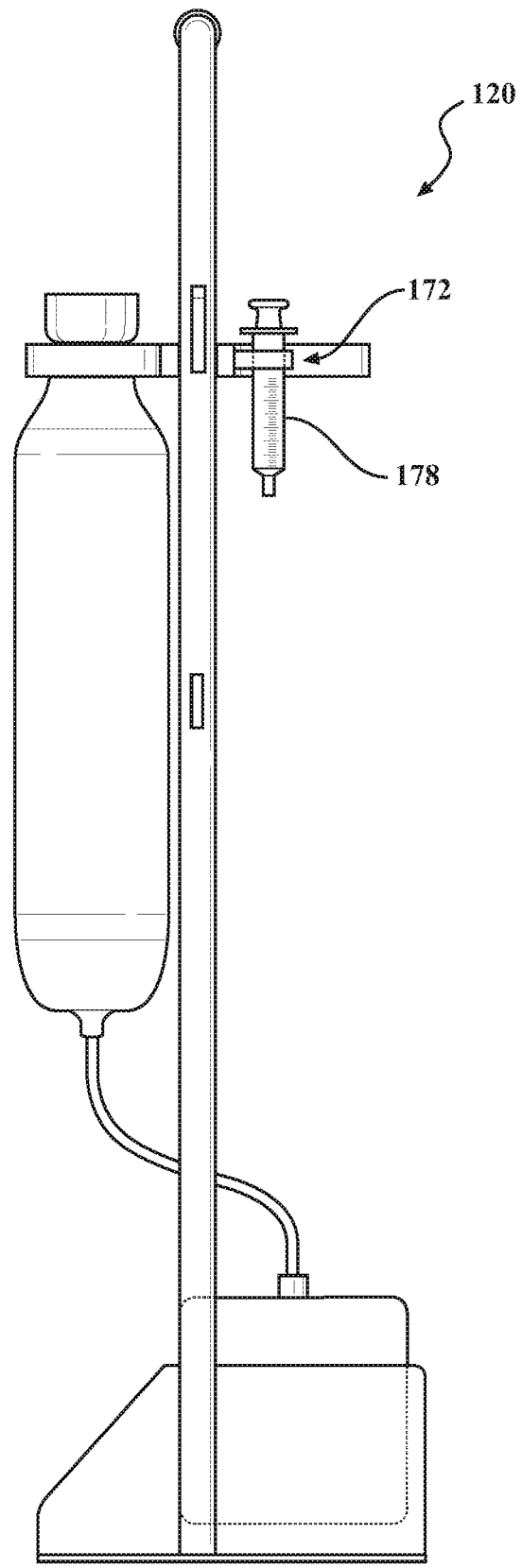
FIG. 9 is a side view of the portable feeding bag holder of FIG. 8.
Figure 10:
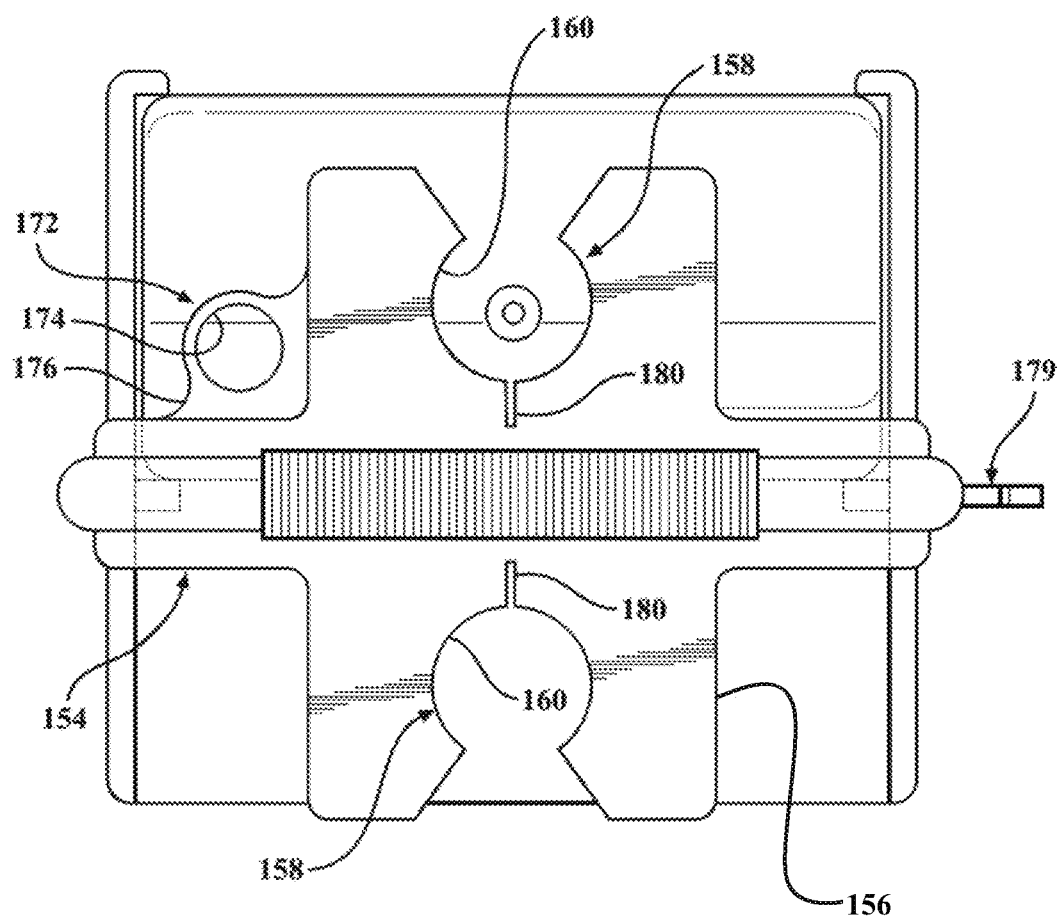
FIG. 10 is a plan view of the portable feeding bag holder of FIG. 8.

Turning next to FIGS. 8-10, in other embodiments the bag holder 120 further includes a syringe holder 172 that is connected to the bracket member 154. Particularly, the syringe holder is an opening 174 (preferably circular) in an extension 176 of the support 156. The opening 174 is sized so that a syringe 178 will not fit completely through the opening so that when a syringe is inserted in the opening from the top, a portion of the syringe cannot pass through the opening, thus leaving the syringe suspended from the bracket member 154. Thus, a user may hold a syringe in the bag holder 120 and can remove and use the syringe as necessary during feeding. Additionally, the tube holder 179 of the bag holder 120 is a flexible, cantilevered member that extends from the side of the frame 144. The tube holder 179 allows for multiple loops of tubing to be hung from the side of the frame 144, when a long length of tubing needs to be wound into loops so that it is off the ground and/or not lying on a surface on which the bag holder 120 is placed. Furthermore, the receiver 158 includes a slit or recessed slot 180 that is continuous with the circular opening 160 and formed by a cut into the wall surface of the circular opening. An edge of a feeding bag may be slid into the slit/slot 180 when the bag is mounted in the receiver 158. The bag holder 120 otherwise has the same structure and features as the bag holder 20.

While the bag holder 20, 120, 220 has been described with reference to the enteral pump 34, the enteral feeding bag 36, and the feeding tube 38, it should be understood that the pump, feeding bag, and tubing are separate elements and do not constitute a part of the bag holder.

The various elements of the components of the bag holder 20, 120, 220 described above, e.g. the base 22, the cradle 32, the frame 44, the handle 48, and the bracket member 54, may be manufactured from, and thus ultimately comprise, the same or different material(s), such as any one or more of the materials described below. Moreover, each element may itself comprise a combination of different materials, and thus may not comprise a homogeneous composition throughout. In certain embodiments, one or more of the components of the bag holder 20, 120, 220 may be monolithic in construction, and may be formed, for example, by injection molding.

In general, materials suitable for use in or as the base 22, the cradle 32, the frame 44, the handle 48, and the bracket member 54 include, wood, metals (e.g. steels, aluminums, alloys, etc.), resins (e.g. thermoset and/or thermoplastic resins), rubbers/elastomers, and combinations thereof. However, myriad materials may be used to manufacture the elements of the bag holder 20, 120, 220, each typically selected as a function of availability, cost, performance/end use applications, etc. Moreover, wood, metals, metal alloys, rubbers/elastomers, and resins are not exhaustive of suitable materials that may be used.

In certain embodiments, the bag holder 20, 120, 220 comprises a resin, such as a thermoplastic and/or thermoset resin. Examples of suitable resins typically comprise the reaction product of a monomer and a curing agent, although resins formed of self-polymerizing monomers (i.e., those acting as both a monomer and a curing agent) may also be utilized. It is to be appreciated that such resins are conventionally named/identified according to a particular functional group present in the reaction product. For example, the term "polyurethane resin" represents a polymeric compound comprising a reaction product of an isocyanate (i.e., a monomer) and a polyol (i.e., a chain extender/curing agent). The reaction of the isocyanate and the polyol create urethane functional groups, which were not present in either of the unreacted monomer or curing agent. However, it is also to be appreciated that, in certain instances, resins are named according to a particular functional group present in the monomer (i.e., a cure site). For example, the term "epoxy resin" represents a polymeric compound comprising a cross-linked reaction product of a monomer having one or more epoxide groups (i.e., an epoxide) and a curing agent. However, once cured, the epoxy resin is no longer an epoxy, or no longer includes epoxide groups, but for any unreacted or residual epoxide groups (i.e., cure sites), which may remain after curing, as understood in the art. In other instances, however, resins may be named according to a functional group present in both the monomer and the reaction product (i.e., an unreacted functional group).

In some embodiments, the various components of the bag holder 20, 120, 220 comprise a material suitable for use under continuous exposure to temperatures of from −40° C. to 120° C., or from −40° C. to 135° C. and/or pressures of from 0.5 to 2 bar. In certain embodiments, one or more, alternatively all, of the various components of the bag holder 20, 120, 220 comprises materials that can withstand up to 30 minutes, alternatively more than 30 minutes, of exposure to temperatures of up to 150° C. without irreversible harmful effects (e.g. melting, etc.).

With regard to composition of the particular components of the bag holder 20, 120, 220 described above comprising a resin, examples of suitable resins include thermoset resins and thermoplastic resins. Examples of suitable thermoset and/or thermoplastic resins typically include polyamides (PA), such as Nylons; polyesters such as polyethylene terephthalates (PET), polybutylene terephthalates (PET), polytrimethylene terephthalates (PTT), polyethylene naphthalates (PEN), liquid crystalline polyesters, and the like; polyolefins such as polyethylenes (PE), polypropylenes (PP), polybutylenes, and the like; styrenic resins; polyoxymethylenes (POM); polycarbonates (PC); polymethylenemethacrylates (PMMA); polyvinyl chlorides (PVC); polyphenylene sulfides (PPS); polyphenylene ethers (PPE); polyimides (PI); polyamideimides (PAI); polyetherimides (PEI); polysulfones (PSU); polyethersulfones; polyketones (PK); polyetherketones (PEK); polyetheretherketones (PEEK); polyetherketoneketones (PEKK); polyarylates (PAR); polyethernitriles (PEN); resol-type; urea (e.g. melamine-type); phenoxy resins; fluorinated resins, such as polytetrafluoroethylenes; thermoplastic elastomers, such as polystyrene types, polyolefin types, polyurethane types, polyester types, polyamide types, polybutadiene types, polyisoprene types, fluoro types, and the like; and copolymers, modifications, and combinations thereof.

With regard to composition of the particular components of the bag holder 20, 120, 220 described above comprising a rubber/elastomer (e.g. the friction material 30), examples of suitable rubber/elastomers include neoprene rubbers, buna-N rubbers, silicone rubbers, ethylene propylene diene monomer (EPDM) rubbers, natural gum rubbers, viton rubbers, natural latex rubbers, vinyl rubbers, santoprene rubbers, epichlorohydrin (ECH) rubbers, butyl rubbers, latex-free thermoplastic elastomer (TPEs), thermoplastic elastomers, hypalon rubbers, ethylene propylene rubbers, fluoroelastomer rubbers, fluorosilicone rubbers, hydrogenated nitrile rubbers, nitrile rubbers, perfluoroelastomer rubbers, polyacrylic rubbers, polychloroprenes, polyurethanes, aflas rubbers (e.g. TFE/Ps), chlorosulfonated polyethelene rubbers, styrene butadiene rubbers (SBRs), polyacrylates, ethylene acrylic rubbers, polyvinyl chloride (PVC), ethylene-vinyl acetate (EVA), and combinations thereof.

In various embodiments, any of the components of the bag holder 20, 120, 220 described above may comprise a material (e.g. a resin, rubber, etc.) including a filler. Examples of suitable fillers include reinforcing fillers added for providing mechanical strength, such as inorganic fillers (e.g. fumed silica fine powder, precipitated silica fine powder, fused silica fined powder, baked silica fine powder, fumed titanium dioxide fine powder, quartz fine powder, calcium carbonate fine powder, diatomaceous earth fine powder, aluminum oxide fine powder, aluminum hydroxide powder, zinc oxide fine powder, zinc carbonate fine powder, glass fibers, etc.), organic fibers (e.g. carbon fibers), natural fibers, and the like, as well as combinations thereof.

It is to be understood that the appended claims are not limited to express and particular structures, compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Further, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. A system comprising:
   a portable feeding bag holder including:
      a planar base having upper and lower surfaces;
      a cradle for receiving an enteral pump, the cradle being disposed on the upper surface of the base;
      a frame extending upwardly from the base, the frame including two vertically extending posts that extend longitudinally away from the base;
      a transverse bracket member extending across the frame, the bracket member being spaced from the base, and the bracket member being connected to the two posts and extending transversely from side-to-side across the frame and between the two posts;
      the bracket member including a support including at least one receiver for suspending an enteral feeding bag therefrom and between the bracket member and the cradle; and
      a handle at a distal end of the frame opposite the base; and
   an enteral feeding bag;
   wherein each receiver is an opening in the support, and the opening is sized to have a diameter that is smaller than a diameter of a collar of the enteral feeding bag.

2. The system of claim 1, wherein the bracket member of the portable feeding bag holder is adjustable along the frame towards and away from the base.

3. The system of claim 1, wherein the at least one receiver of the support of the portable feeding bag holder is two receivers.

4. The system of claim 3, wherein the receivers of the portable feeding bag holder are positioned towards a front and a back of the feeding bag holder.

5. The system of claim 3, wherein the receivers of the portable feeding bag holder are aligned in a direction perpendicular to a transverse direction across the frame.

6. The system of claim 1, wherein each receiver of the portable feeding bag holder is an opening in the support.

7. The system of claim 6, wherein each receiver of the portable feeding bag holder is defined by a semi-circular slot.

8. The system of claim 1, wherein the base of the portable feeding bag holder is weighted.

9. The system of claim 1, wherein the portable feeding bag holder includes a tube holder disposed on a side of the frame.

10. The system of claim 9, wherein the tube holder of the portable feeding bag holder is a hook.

11. The system of claim 9, wherein the tube holder of the portable feeding bag holder includes a slot facing away from the base.

12. The system of claim 1, wherein the lower surface of the base of the portable feeding bag holder includes a friction material.

13. The system of claim 12, wherein the friction material of the base of the portable feeding bag holder is one of rubber and silicone.

14. The system of claim 12, wherein the friction material on the lower surface of the base of the portable feeding bag holder includes an anti-slip pattern.

15. The system of claim 10, wherein a length of the frame of the portable feeding bag holder from the base to the handle is greater than a length of the bracket member in the transverse direction.

16. The system of claim 10, wherein the support of the bracket member of the portable feeding bag holder does not extend beyond a footprint of the portable feeding bag holder.

17. A system comprising:
  a portable feeding bag holder including:
    a planar base having upper and lower surfaces;
    a cradle for receiving an enteral pump, the cradle being disposed on the upper surface of the base;
    a frame extending upwardly from the base, the frame including two vertically extending posts that extend longitudinally away from the base;
    a transverse bracket member extending across the frame, the bracket member being spaced from the base, and the bracket member being connected to the two posts and extending transversely from side-to-side across the frame and between the two posts;
    the bracket member including a support including at least one receiver for suspending an enteral feeding bag therefrom and between the bracket member and the cradle; and
    a handle at a distal end of the frame opposite the base; and
  an enteral feeding bag;
  wherein a distance from the base to the bracket member is greater than a length of the enteral feeding bag that is suspended from the support.

18. A method of transporting an enteral feeding bag, the method comprising:
  providing a system comprising:
    an enteral feeding bag; and
    a portable feeding bag holder including:
      a planar base having upper and lower surfaces;
      a cradle for receiving an enteral pump, the cradle being disposed on the upper surface of the base;
      a frame extending upwardly from the base, the frame including two vertically extending posts that extend longitudinally away from the base;
      a transverse bracket member extending across the frame, the bracket member being spaced from the base, and the bracket member being connected to the two posts and extending transversely from side-to-side across the frame and between the two posts;
      the bracket member including a support including at least one receiver for suspending the enteral feeding bag therefrom and between the bracket member and the cradle; and
      a handle at a distal end of the frame opposite the base;
      wherein each receiver is an opening in the support, and the opening is sized to have a diameter that is smaller than a diameter of a collar of the enteral feeding bag;
      wherein the base of the portable feeding bag holder is positioned on a surface at a first location;
  the method further comprising the steps of:
  mounting the enteral feeding bag on the portable feeding bag holder;
  lifting the portable feeding bag holder by the handle and off the surface;
  carrying the portable feeding bag holder by the handle to move the portable feeding bag holder from the first location to a different, second location; and
  setting the base of the portable feeding bag holder down onto a surface at the second location.

* * * * *